(12) United States Patent
Shimizu et al.

(10) Patent No.: US 11,566,267 B2
(45) Date of Patent: Jan. 31, 2023

(54) METHOD FOR PRODUCING ORGANIC SUBSTANCE

(71) Applicant: SEKISUI CHEMICAL CO., LTD., Osaka (JP)

(72) Inventors: Satoshi Shimizu, Tsukuba (JP); Kokoro Hamachi, Tsukuba (JP); Kazuto Natsuyama, Tsukuba (JP); Kanetomo Sato, Tsukuba (JP)

(73) Assignee: SEKIGUJI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 16/981,076

(22) PCT Filed: Mar. 3, 2019

(86) PCT No.: PCT/JP2019/012237
§ 371 (c)(1),
(2) Date: Sep. 15, 2020

(87) PCT Pub. No.: WO2019/188838
PCT Pub. Date: Oct. 3, 2019

(65) Prior Publication Data
US 2021/0024963 A1    Jan. 28, 2021

(30) Foreign Application Priority Data

Mar. 26, 2018 (JP) .............................. JP2018-058455
Mar. 26, 2018 (JP) .............................. JP2018-058897

(51) Int. Cl.
*C12P 7/08* (2006.01)

(52) U.S. Cl.
CPC ...................................... *C12P 7/08* (2013.01)

(58) Field of Classification Search
None
See application file for complete search history.

(56) References Cited

U.S. PATENT DOCUMENTS

2016/0198737 A1* 7/2016 Shirota .................. A23J 1/001
426/495

FOREIGN PATENT DOCUMENTS

| JP | 57-208993 A | 12/1982 |
|---|---|---|
| JP | 2011-177159 A | 9/2011 |
| JP | 2015-053866 A | 3/2015 |
| JP | 2016-029921 A | 3/2016 |
| WO | 2016/017573 A1 | 2/2016 |
| WO | 2017/221987 A1 | 12/2017 |

OTHER PUBLICATIONS

Machine translation of JP 2016-029921 A, 7 pages, obtained from Google Patents on Jul. 12, 2021 (Year: 2021).*
Stanbury et al., "Principles of Fermentation", Chapter 10, "The recovery and purification of fermentation products", pp. 619-686, Elsevier, New York, Jan. 2017 (Year: 2017).*
Communication, dated Oct. 8, 2020, issued in International Application No. PCT/JP2019/012237.
Michael Köpke et al., "Clostridium Ijungdahlii represents a microbial production platform based on syngas", Proc Natl Acad Sci USA, Jul. 20, 2010, pp. 13087-13092, vol. 107, No. 29.
Notice of Reasons for Refusal, dated Apr. 21, 2020, issued by the Japanese Patent Office in corresponding Japanese Application No. 2019-544753.
International Search report for PCT/JP2019/012237, dated May 21, 2019.
Extended European Search Report, dated Nov. 30, 2021, issued by the European Patent Office in European Patent Application No. 19777155.3.

* cited by examiner

*Primary Examiner* — David Steadman
(74) *Attorney, Agent, or Firm* — Sughrue Mion, PLLC (57) ABSTRACT

Provided is a method for producing an organic substance from a syngas by microbial fermentation, wherein only the solid component can be efficiently separated from an organic substance-containing liquid obtained by microbial fermentation to reduce the content of microorganisms, etc. Disclosed is a method for producing an organic substance from a syngas containing carbon monoxide by microbial fermentation, which comprises a microbial fermentation step wherein the syngas is fed to a microbial fermenting vessel and a liquid containing an organic substance is obtained by microbial fermentation, a solid-liquid separation step wherein the organic substance-containing liquid is separated into a solid component containing microorganisms and a liquid component containing an organic substance, and an extraction step wherein the organic substance-containing liquid is extracted from the liquid component, wherein the organic substance-containing liquid is heated to 40° C. or higher and then subjected to a centrifugal separation operation.

5 Claims, 3 Drawing Sheets

METHOD FOR PRODUCING ORGANIC SUBSTANCE

CROSS-REFERENCE TO RELATED APPLICATIONS

This application is a National Stage of International Application No. PCT/JP2019/012237 filed Mar. 22, 2019, claiming priority based on Japanese Patent Application Nos. 2018-058455 and 2018-058897 filed on Mar. 26, 2018; the entire contents of which are incorporated herein by reference.

BACKGROUND OF THE INVENTION

Field of the Invention

The present invention relates to a method for producing an organic substance. In particular, the present invention relates to a method for producing an organic substance using a fermentation liquid obtained by microbial conversion of a specific syngas.

Background Art

In recent years, methods for producing various organic substances from raw materials other than petroleum, for example, methods for producing bioethanol from edible raw materials such as corn by a sugar fermentation method have been of interest from the viewpoint of concerns about depletion of fossil fuel resources due to mass consumption of oil and alcohol produced from petroleum, and global environmental problems such as increase of carbon dioxide in the atmosphere. However, the sugar fermentation method using such edible raw materials has a problem of bringing about price escalation of food, for example, since the limited farmland area will be used for the production of other than food.

In order to solve such problem, investigations are made to various methods for producing various organic substances which have been conventionally produced from petroleum, using non-edible raw materials which have been disposed. For example, Michael Koepke et al. proposed microbial species and metabolic systems that convert carbon dioxide, carbon monoxide, and hydrogen-containing syngas to acetic acid and ethanol ("*Clostridium ljungdahlii* represents a microbial production platform based on syngas", Proc Natl Acad Sci USA, Aug. 24, 2010, vol. 107, no. 29, 13087-13092). Japanese Patent Laid-Open Publication No. 2015-53866 also discloses a method for producing ethanol by microbial fermentation from iron and steel exhaust gas, syngas obtained by gasification of waste, and the like.

In a method for producing ethanol from syngas by microbial fermentation, since ethanol produced by microbial fermentation is contained in the microbial fermenting vessel, there is a need to extract ethanol therefrom. For example, WO2017/221987 discloses that organic substances in high-purity, particularly ethanol, are obtained by gasifying waste, subsequently producing an organic substance-containing liquid by microbial fermentation using the gas, and thereafter purifying the organic substance-containing liquid by a distillation device.

In a method for producing an organic substance using a microorganism, for example, Japanese Patent Laid-Open Publication No. 2011-177159 proposes a method for removing a protein remaining in a lactic fermentation liquid, in which the protein is aggregated by heat denaturation and the aggregated substance is removed by solid-liquid separation, as one method for isolating and purifying a desired organic substance.

SUMMARY OF THE INVENTION

Problem to be Solved

The organic substance-containing liquid obtained by the above-described microbial fermentation contains a large amount of microorganisms and the dead microorganisms apart from the desired organic substances. Therefore, when the organic substance-containing liquid is introduced as it is into a distillation device or the like, the solid components such as the microorganisms increases its concentration as the organic substances are distilled off, and as a result, the viscosity of the organic substance-containing liquid in the distillation device increases, which may hinder continuous operation. Therefore, it is necessary to separate the organic substance-containing liquid into the liquid component and the solid component and to remove the solid component such as the microorganisms before the distillation operation. As such a solid-liquid separation means, a membrane separation device and a centrifugal separation device have been conventionally known; however since the filter in the membrane separation device generates clogging, it is necessary to periodically clean and replace the filter, and thus solid-liquid separation was difficult in a continuous manner. Further, in the centrifugation device, since the solid component such as the microorganisms contained in the organic substance-containing liquid is very small, there was a problem that the solid component and the liquid component cannot be sufficiently separated.

In order to solve the above-mentioned in order to solve the above-mentioned problem and as a result of investigation by the present inventors of a method for separating a solid liquid in an organic substance-containing liquid comprising microorganisms, the present inventors have obtained the knowledge that by performing centrifugal separation after heating the organic substance-containing liquid, it is possible to efficiently separate the solid components such as the microorganisms and the dead microorganisms from the organic substance-containing liquid. It is therefore an object of the present invention to provide a method for producing an organic substance from a syngas by microbial fermentation, wherein only a solid component containing microorganisms and the like can be efficiently separated from an organic substance-containing liquid obtained by microbial fermentation.

Means for Solving the Problem

As a result of examination by the present inventors in view of the above problems, it was found that heating an organic substance-containing liquid obtained from microbial fermentation at a specific temperature and then performing centrifugal separation makes it possible to efficiently separate only solid components such as microorganisms from the organic substance-containing liquid and reduce the content of the microorganisms. That is, the overview of the present invention is as follows.

[1] A method for producing an organic substance from a syngas comprising carbon monoxide by microbial fermentation, comprising:

a microbial fermentation step of feeding a syngas to a microbial fermenting vessel and obtaining the organic substance-containing liquid by the microbial fermentation, a solid-liquid separation step of separating the organic substance-containing liquid into a solid component containing microorganisms and a liquid component containing the organic substance, and an extraction step of extracting the organic substance from the liquid component, wherein the organic substance-containing liquid is heated to 40° C. or higher and then subjected to a centrifugal separation operation in the solid-liquid separation step.

[2] The method according to [1], wherein the syngas is obtained by gasifying a carbon source.

[3] The method according to [1] or [2], wherein the carbon source is waste.

[4] The method according to any one of [1] to [3], wherein the organic substance contains an alcohol having 1 to 6 carbons.

[5] The method according to any one of [1] to [4], wherein the microorganism is *Clostridium*.

[6] The method according to any one of [1] to [5], wherein the centrifugal separation operation is performed at a centrifugal acceleration of 100 to 10000 G.

[7] The method according to any one of [1] to [6], wherein the organic substance-containing liquid is heated at a temperature of 45° C. or more and less than 70° C.

[8] The method according to any one of [1] to [7], wherein the organic substance is extracted by purification from the liquid component in the extraction step.

[9] A method for producing an organic substance by supplying a fixed amount of a syngas containing 10 vol % or more of carbon monoxide to a microbial fermenting vessel and subjecting said syngas to microbial fermentation with microorganisms, wherein when the amount of syngas to be supplied to the fermentation tank decreases or the supply of the syngas is temporarily suspended, a life sustaining gas containing 15 vol % or more of carbon dioxide is supplied to said microbial fermenting vessel.

Effect of the Invention

According to the present invention, when an organic substance-containing liquid obtained by microbial fermentation is separated into a solid component containing microorganisms, dead microorganisms, etc., and a liquid component containing an organic substance by a centrifugal separation operation, the solid component containing microorganisms, etc., can be efficiently separated by heating the organic substance-containing liquid to a specific temperature or higher. Therefore, the organic substance can be continuously produced from the liquid component without interrupting the extraction step.

EMBODIMENT OF THE INVENTION

Hereinafter, one example of a preferred embodiment of the present invention will be described. However, the following embodiments are examples for illustrating the present invention, and the present invention is not limited in any way by the following embodiments. In the present specification, the proportion of each component in the gas is a proportion based on volume, not weight, unless otherwise specified. Thus, unless otherwise specified, percent by 100 represents percent by volume and ppm represents ppm by volume.

Figure 1:
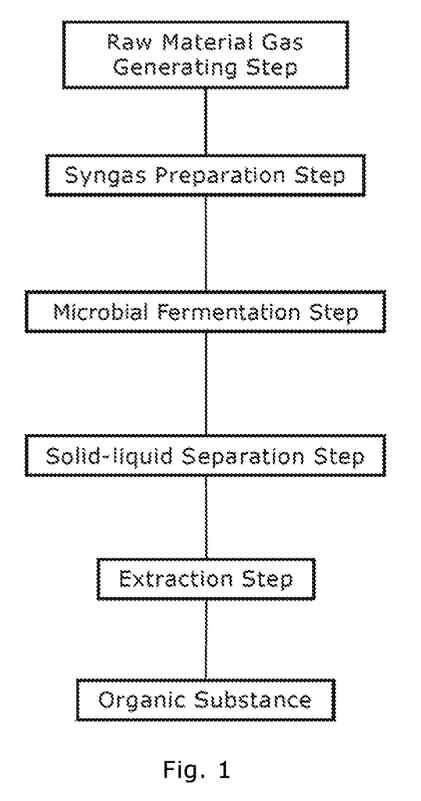
FIG. 1 is a figure of a process flow illustrating one example of the method for producing an organic substance according to the present invention.
Figure 2:
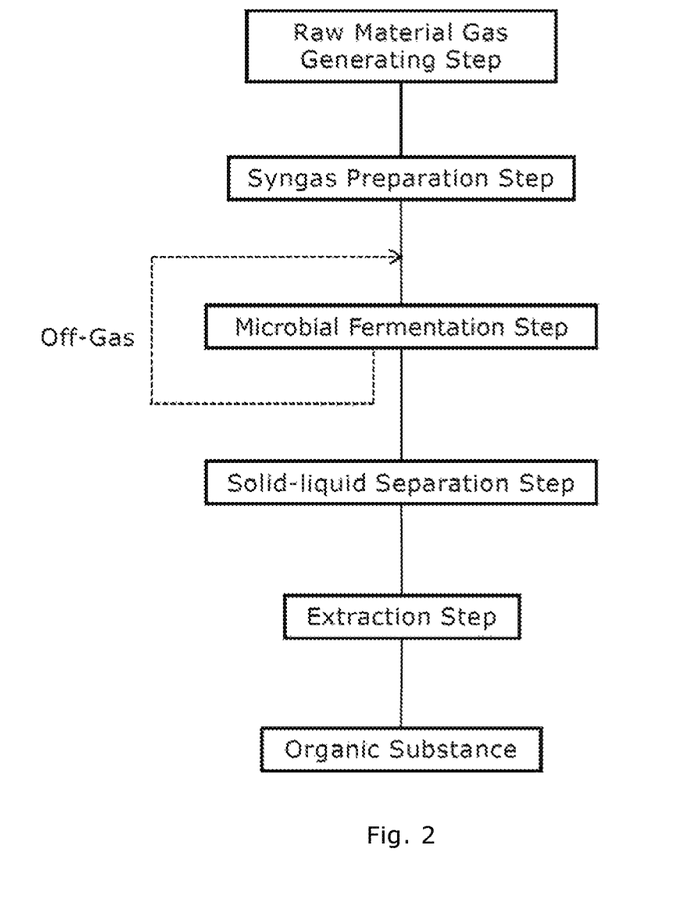
FIG. 2 is a figure of a process flow illustrating another example of the method for producing an organic substance according to the present invention.

A method for producing an organic substance according to the present invention will be described with reference to the drawings. FIGS. 1 and 2 are figures of process flows showing a method for producing an organic substance according to an embodiment of the present invention. A method for producing an organic substance according to one embodiment of the present invention comprises a microbial fermentation step of supplying a syngas comprising carbon monoxide to a microbial fermenting vessel and obtaining an organic substance-containing liquid by microbial fermentation; a solid-liquid separation step of separating the organic substance-containing liquid into a solid component containing microorganisms and a liquid component containing an organic substance; and an extraction step of extracting the organic substance from the liquid component.

The method for producing an organic substance according to another embodiment of the present invention may include, as shown in FIG. 2, a step of supplying the life sustaining gas to the microbial fermenting vessel when the amount of syngas to be supplied to the fermentation tank decreases or the supply of the syngas is temporarily suspended.

The method for producing an organic substance of the present invention may further include a raw material gas generating step, a syngas preparing step, a water recycling step, and the like, if necessary.

Each step will be described below.

<Raw Material Gas Generating Step>

The raw material gas generating step is a step of generating a raw material gas by gasifying a carbon source in the gasification unit (see FIG. 1). A gasification furnace may be used in the raw material gas generating step.

A gasification furnace is a furnace for burning (incompletely burning) a carbon source, examples thereof including a shaft furnace, a kiln furnace, a fluidized bed furnace, and a gasification reforming furnace. The gasification furnace is preferably a fluidized bed furnace type because a high hearth load and excellent operability can be achieved by partially combusting the waste. The waste is gasified in a fluidized bed furnace at a low temperature (about 450 to 600° C.) and in a low oxygen atmosphere to be decomposed into char containing a large amount of gas (carbon monoxide, carbon dioxide, hydrogen, methane, etc.) and carbon. In addition, since the incombustibles contained in the waste are separated from the bottom of the furnace in a hygienic and lightly oxidized state, valuable substances such as iron and aluminum in the incombustibles can be selectively recovered. Therefore, gasification of such waste enables efficient resource recycling.

The gasification temperature in the raw material gas generating step is usually 100° C. to 1500° C., preferably 200° C. to 1200° C.

The reaction time for gasification in the raw material gas generating step is usually 2 seconds or more and preferably 5 seconds or more.

<Carbon Source>

A carbon source used in the raw material gas generating step is not particularly limited, and for example, suitably used are coal used in a coke oven in a steel plant, a blast furnace (blast furnace gas), a converter or a coal-fired power plant, general waste and industrial waste introduced into an incinerator (especially a gasification furnace), carbon dioxide produced as a by-product by various industries, and also various carbon-containing materials and the like for the purpose of recycling.

More specifically, the carbon source includes plastic waste, kitchen waste, municipal solid waste (MSW), waste tires, biomass waste, household waste such as duvet (futon) and paper, waste such as building materials, coal, petroleum, petroleum-derived compounds, natural gas, shale gas, and the like, among which various types of waste are preferable, and from the viewpoint of separation cost, the more preferred is unsorted municipal waste.

<Raw Material Gas>

The raw material gas obtained by gasifying a carbon source contains carbon monoxide and hydrogen as essential components, and may further contain carbon dioxide, oxygen and nitrogen. As other components, the raw material gas may further contain components such as soot, tar, a nitrogen compound, a sulfur compound, a phosphorus compound, and an aromatic compound.

The raw material gas may be produced as a gas containing 20 vol % or more of carbon monoxide by performing heat treatment (commonly known as: gasification) for burning (incompletely burning) a carbon source in the raw material gas generating step, that is, by partially oxidizing the carbon source.

<Syngas Preparation Step>

The raw material gas as above may be supplied to the microbial fermenting vessel as a syngas as it is; however, the syngas may be prepared so as to be suitable for the microbial fermentation. When the raw material gas is derived from waste, the raw material gas tends to contain carbon monoxide in an amount of 20 vol % to 80 vol %, carbon dioxide in an amount of 10 vol % to 40 vol %, hydrogen in an amount of 10 vol % to 80 vol %, a nitrogen compound in an amount of 1 ppm or more, a sulfur compound in an amount of 1 ppm or more, a phosphorus compound in an amount of 0.1 ppm or more and/or an aromatic compound in an amount of 10 ppm or more. It may also contain substances such as other environmental contaminants, soot and dust particles, and impurities. Therefore, when the syngas is supplied to the microbial fermenting vessel, it is preferable to reduce or remove substances that are unfavourable for stable culturing of microorganisms and compounds in an undesirable amount, and the like from the raw material gas so that the content of each component contained in the raw material gas is in a range suitable for stable culturing of microorganisms. In particular, since many aromatic compounds have cytotoxicity, it is preferable to reduce and remove the compounds from the raw material gas.

That is, the syngas preparation step is a step of removing or reducing a specific substance such as various contaminants, soot and dust particles, impurities, and undesirable amounts of compounds from the raw material gas (see FIG. 1). In the pretreatment step, syngas may be obtained from the raw material gas. The pretreatment step can be carried out using one or two or more of, for example, a scrubber (a water-soluble impurity separator), a gas chiller (a water separator), a cyclone, a particulate (soot) separator such as a bag filter, a desulfurizer (a sulfide separator), a low-temperature (cryogenic) separator, a membrane separator, a pressure swing adsorption separator (PSA), a temperature swing adsorption separator (TSA), a pressure temperature swing adsorption separator (PTSA), a deoxygenator, a separator using activated carbon, a deoxygenator, and more specifically, a separator using a copper or a palladium catalyst.

<Syngas>

The syngas used in the present invention contains at least carbon monoxide as an essential component and may further contain hydrogen, carbon dioxide, and nitrogen.

The syngas used in the present invention may be a gas obtained by carrying out the steps of gasifying a carbon source to generate a raw material gas (a raw material gas generating step), and then adjusting the concentration of each component of carbon monoxide, carbon dioxide, hydrogen, and nitrogen and reducing or removing the above-mentioned substances and compounds from the raw material gas.

The concentration of carbon monoxide in the syngas is usually 10 vol % to 80 vol %, preferably 20 vol % to 50 vol %, more preferably 25 vol % to 48 vol %, and particularly preferably 35 vol % to 45 vol % with respect to the total concentration of carbon monoxide, carbon dioxide, hydrogen and nitrogen in the syngas.

The concentration of hydrogen in the syngas is usually 10 vol % to 80 vol % or less, preferably 30 vol % to 55 vol %, and more preferably 40 vol % to 50 vol % with respect to the total concentration of carbon monoxide, carbon dioxide, hydrogen, and nitrogen in the syngas.

The concentration of carbon dioxide in the syngas is usually 0.1 vol % to 40 vol %, preferably 0.3 vol % to 30 vol %, more preferably 0.5 vol % to 10 vol %, and particularly preferably 1 vol % to 6 vol %, with respect to the total concentration of carbon monoxide, carbon dioxide, hydrogen, and nitrogen in the syngas.

The concentration of nitrogen in the syngas is usually 40 vol % or less, preferably 1 vol % to 20 vol % or less, and more preferably 5 vol % to 15 vol % with respect to the total concentration of carbon monoxide, carbon dioxide, hydrogen, and nitrogen in the syngas.

The concentration of carbon monoxide, carbon dioxide, hydrogen, and nitrogen can be set within a predetermined range by changing the C—H—N element composition of the carbon source in the raw material gas generating step or by changing the combustion conditions such as the combustion temperature and the oxygen concentration of the supply gas during combustion if necessary. For example, in the case where the concentration of carbon monoxide or hydrogen is to be changed, a carbon source having a high C—H ratio such as waste plastic may be used, and in the case where the concentration of nitrogen is to be lowered, a gas having a high oxygen concentration may be supplied in the raw material gas generating step.

The syngas used in the present invention may contain a sulfur compound, a phosphorus compound, a nitrogen compound and the like in addition to the above components. The content of each of these compounds is preferably 0.05 ppm or more, more preferably 0.1 ppm or more, further preferably 0.5 ppm or more, and also preferably 80 ppm or less, more preferably 60 ppm or less, and further preferably 40 ppm or less. When the content of the sulfur compound, the phosphorus compound, the nitrogen compound, and the like is not less than the lower limit, there is an advantage that the microorganisms can be suitably cultured, and when the content is not more than the upper limit, there is an advantage that the culture medium is not contaminated by various nutrition sources which the microorganisms have not consumed.

Examples of the sulfur compound include sulfur dioxide, $CS_2$, COS, and $H_2S$, and preferred amongst them are $H_2S$ and sulfur dioxide as they are easily consumed as a nutrition source for the microorganisms. Therefore, it is more preferable that the syngas contains the sum of $H_2S$ and sulfur dioxide within the above ranges.

As the phosphorus compound, phosphoric acid is preferred as it is easily consumed as a nutrition source for the microorganisms. Therefore, it is more preferable that the syngas contains phosphoric acid within the above ranges.

Examples of the nitrogen-containing compound include nitrogen monoxide, nitrogen dioxide, acrylonitrile, acetonitrile, HCN, and the like, and HCN is preferable in that it is easily consumed as a nutrient source for the microorganisms. Therefore, it is more preferable that the syngas contains HCN in the above range.

The syngas may contain an aromatic compound in the amount of 0.01 ppm to 90 ppm, preferably 0.03 ppm or more, more preferably 0.05 ppm or more, and further preferably 0.1 ppm or more, and preferably 70 ppm or less, more preferably 50 ppm or less, and further preferably 30 ppm or less. When the content is not less than the lower limit, the microorganisms tend to be cultured suitably, and when the content is not more than the upper limit, the culture medium tends to be less contaminated by various nutrition sources which the microorganisms have not consumed.

<Supplying Syngas to Microbial Fermenting Vessel>

The syngas supplying step is a step of supplying the syngas obtained as described above into a microbial fermenting vessel containing a microbial culture solution (see FIG. 2). As long as the component conditions of the syngas are satisfied, the gas obtained through the raw material gas generating step may be used as it is as the syngas, or the syngas may be used by adding another predetermined gas to the gas obtained by reducing or removing impurities and the like from the raw material gas. As another predetermined gas, for example, at least one of the compounds selected from the group consisting of sulfur compounds such as sulfur dioxide, phosphorus compounds, and nitrogen compounds may be added to form a syngas.

The syngas is supplied to the microbial fermenting vessel in a fixed amount to be subjected to microbial fermentation. In the present invention, a fixed amount does not mean that the amount of the syngas to be supplied is exactly the specific amount, and the amount of the syngas to be fed may be appropriately adjusted according to the desired amount of the organic substance to be produced and the concentration of the microbial culture solution in the microbial fermenting vessel. That is, in the present invention, the "fixed amount" is intended to exclude the case where the feed amount of the syngas decreases, or the supplying of the syngas is temporarily suspended. Further, in the present invention, the case where the feed amount of the syngas decreases means the case where the average feed amount of the syngas fed to the microbial fermenting vessel is 60% or less.

In the present invention, when the syngas fed in a fixed amount reduces or temporarily suspends, a life sustaining gas containing 15 vol % or more of carbon dioxide is supplied to the microbial fermenting vessel. When the feed of syngas to the microbial fermenting vessel is reduced or temporarily suspended, the feed of microbial nutrients (such as carbon monoxide) decreases, and nearly half of the microorganisms in the microbial fermenting vessel die in a few hours. The present inventors have found that even when the feed of a nutrient source (carbon monoxide or the like) for the microorganisms is reduced or suspended, the microorganisms are suppressed from dying by feeding a gas containing carbon dioxide in a predetermined concentration or more to a microorganism fermentation tank as a life sustaining gas. The reason for this is not clear; however, it is presumed as follows. Microorganisms that have a COA metabolic cycle have a circuit that converts carbon dioxide into acetic acid and target organic substances, and normally, a metabolic system is the main circuit that uses carbon monoxide as a raw material (nutrient) as it is more efficient; however, in a state of nutrient depletion, a secondary circuit that uses carbon dioxide as a raw material (nutrient) functions instead of the main circuit. Therefore, when the feed of syngas containing 10 vol % or more of carbon monoxide is reduced or temporarily suspended, the COA circuit mainly uses the secondary circuit by supplying a gas containing a fixed concentration of carbon dioxide to the microbial fermenting vessel, and the cells can survive without dying.

The life sustaining gas may contain carbon monoxide, hydrogen, nitrogen, and the like in addition to carbon dioxide; however, the concentration of carbon dioxide must be 15 vol % or more. From the viewpoint of extending the life of microorganisms, the concentration of carbon dioxide in the life sustaining gas is preferably 25 vol % to 60 vol % and more preferably 30 vol % to 50 vol %.

As the life sustaining gas, an off-gas generated by a microbial fermentation step described later may be used (see FIG. 2). For example, when microbial fermentation is carried out using a syngas containing 10 vol % or more of carbon monoxide and less than 15 vol % of carbon dioxide, the off-gas can be suitably used as a life sustaining gas since the off-gas generated contains less than 10 vol % of carbon monoxide and 15 vol % or more of carbon dioxide. When the off-gas is used as the life sustaining gas, the concentration of carbon monoxide in the life sustaining gas is preferably less than 12 vol % and more preferably 4 vol % to 10 vol %.

<Microbial Fermentation Step>

The microbial fermentation step is a step of producing an organic substance by microbial fermentation of the above-described syngas in a microbial fermenting vessel (see FIG. 1). The microbial fermenting vessel is preferably a continuous fermenter. In general, the microbial fermenting vessel may be of any shape, including a stirred type, an airlift type, a bubble column type, a loop type, an open-bond type, and a photobio type.

As the syngas to be supplied to the microbial fermenting vessel, the gas obtained through the raw material gas generating step may be used as it is as long as the composition conditions of the syngas are satisfied, or the syngas may be used by adding another predetermined gas to the gas obtained by reducing or removing impurities and the like from the raw material gas. As another predetermined gas, for example, at least one of the compounds selected from the group consisting of sulfur compounds such as sulfur dioxide, phosphorus compounds, and nitrogen compounds may be added to form a syngas.

Although the syngas and the microbial culture solution may be continuously fed to the microbial fermenting vessel, the syngas and the microbial culture solution need not be fed simultaneously, and the syngas may be fed to the microbial fermenting vessel to which the microbial culture solution has been previously fed. It is known that some anaerobic microorganisms produce organic substances which are valuables such as ethanol, from a substrate gas such as the syngas by the fermenting action, and these gas-utilizing microorganisms are cultured in a liquid medium. For example, the liquid medium and the gas-utilizing bacteria may be fed and stored, and while the liquid medium is stirred in this state, the syngas may be fed into the microbial fermentation vessel. Accordingly, the gas-utilizing bacteria can be cultured in a liquid medium and by the fermenting action, an organic substance can be produced from the syngas.

<Microorganisms>

The microorganisms (species) contained in the microbial culture solution are not particularly limited as long as they can produce a desired organic substance by microbial fermentation of syngas using carbon monoxide as a main raw material. For example, the microorganisms (species) are preferably microorganisms which generate an organic substance from the syngas by the fermenting action of gas-utilizing bacteria, and particularly preferably microorganisms having a metabolic pathway of acetyl COA. Among the gas-utilizing bacteria, the genus *Clostridium* is more preferred, and *Clostridium autoethanogenum* is particularly preferred, without particular limitation. The following is a further example.

Gas-utilizing bacteria include both eubacteria and archaebacteria. Examples of the eubacteria include *Clostridium, Moorella, Acetobacterium, Carboxydocella, Rhodopseudomonas, Eubacterium, Butyribacterium, Oligotropha, Bradyrhizobium*, and aerobic hydrogen-oxidizing bacteria, Ralsotonia bacteria, and the like.

On the other hand, examples of the archaebacteria include bacteria from the genus of *Methanobacterium, Methanobrevibacter, Methanocalculus, Methanococcus, Methanosarcina, Methanosphaera, Methanothermobacter, Methanothrix, Methanoculleus, Methanofollis, Methanogenium, Methanospirillium, Methanosaeta, Thermococcus, Thermofilum, Arcaheoglobus*, and the like. Amongst these, preferred as the archaebacterial are *Methanosarcina, Methanococcus*, Methanothermobacter, Methanothrix, *Thermococcus*, Thermofilum, and *Archaeoglobus*.

Further, preferred as the archaebacteria are bacteria from the genus of *Methanosarcina, Methanothermobactor*, or *Methanococcus*, and particularly preferred are *Methanosarcina* or *Methanococcus*, due to excellent carbon monoxide and carbon dioxide utilizing properties. Specific examples of the bacteria from the genus of *Methanosarcina* include *Methanosarcina barkeri, Methanosarcina mazei, Methanosarcina acetivorans*, and the like.

Among the above gas-utilizing bacteria, bacteria having a high ability to produce organic substances of interest are selected and used. For example, the gas-utilizing bacteria having a high ethanol-producing ability include *Clostridium autoethanogenum, Clostridium I jungdahlii, Clostridium aceticum, Clostridium carboxidivorans, Moorella thermoacetica, Acetobacterium woodii*, and among these, *Clostridium autoethanogenum* is particularly preferable.

The medium used for culturing the above-described microorganisms (species) is not particularly limited, as long as it has an appropriate composition corresponding to the microorganisms, and is a liquid containing water as a main component and a nutrient (for example, vitamin, phosphoric acid, etc.) dissolved or dispersed in the water.

<Solid-Liquid Separation Step>

The solid-liquid separation step of the present invention is a step of separating the organic substance-containing liquid obtained in the microbial fermentation step as above into a solid component mainly composed of microorganisms and a liquid component containing an organic substance (see FIG. 1). That is, since the organic substance-containing liquid obtained in the microbial fermentation step contains not only the desired organic substance but also microorganisms contained in the microbial fermenting vessel and dead microorganisms, etc., a solid-liquid separation step is carried out in order to remove the solid components such as the microorganisms. Generally, a membrane separation means and a centrifugal separation means are known as an operation means for performing solid-liquid separation, and in the present invention, a solid-liquid separation step is performed by the centrifugal separation means.

In the present invention, centrifugal separation operation is carried out when the organic substance-containing liquid obtained in the microbial fermentation step is separated into a solid component containing the microorganisms, dead microorganisms, and the like, and a liquid component containing the organic substance by means of centrifugal separation, after the organic substance-containing liquid is heated to 40° C. or higher. By subjecting the organic-substance-containing liquid heated to 40° C. or higher to the centrifugal separation operation, it is possible to efficiently separate the solid component including the microorganisms and the like. Therefore, the foaming of the liquid component in the step of extracting the organic substance from the liquid component can be suppressed, and the organic substance can be continuously produced from the liquid component without interrupting the extraction step. The reason is not clear; however, it can be presumed as follows.

The performance of solid-liquid separation by the centrifugal operation is known to affect the weight of the solid component. The organic substance-containing liquid obtained by microbial fermentation contains microorganisms and the dead microorganisms in a dispersed state. Many of these microorganisms etc. do not have sufficient weight to be separated by centrifugation, and even when the liquid containing the organic substance is subjected to centrifugation, a part of the microorganisms and the dead microorganisms remain in the liquid component after the centrifugation. Therefore, when distillation is carried out at the time of extracting the desired organic substance from the liquid component after the solid-liquid separation, the concentration of the solid component remaining in the liquid component increases along with the evaporation of the organic substance and the viscosity of the liquid component rises, which hinders the continuous distillation operation. In the present invention, by heating the organic substance-containing liquid to 40° C. or higher before carrying out the centrifugal separation, microorganisms and the like contained in the organic substance-containing liquid gather together to form an aggregate, thereby increasing the weight, allowing the solid components to be efficiently separated, and a liquid component having an extremely small residual amount of the microorganisms and the like can be obtained. Therefore, it is considered that the viscosity increase of the liquid component can be suppressed when a desired organic substance is extracted from the liquid component, and as a result, continuous distillation can be performed, and the desired organic substance can be efficiently extracted. It is considered that this is because proteins attached to the cell membrane or the cell membrane surface of the microorganism, etc. are denatured by heating, and the microorganisms, etc. are gathered together to form aggregates. For example, in *Clostridium* microorganisms, proteins attached to the cell membrane undergo denaturation at around 40° C., and the microorganisms in contact begin to aggregate.

From the viewpoint of efficiently separating the solid component (microorganism or the like) and the liquid component, the heating temperature of the organic substance-containing liquid is 40° C. or higher, preferably 45° C. or higher, more preferably 48° C. or higher, further preferably 50° C. or higher, and particularly preferably 55° C. or higher. Although the upper limit of the heating temperature varies depending on the organic substance, etc. contained in the organic substance-containing liquid, the upper limit may be a temperature at which the organic substance does not denature or evaporate, and is usually 120° C. or less, preferably 100° C. or less, more preferably 80° C. or less, further preferably 75° C. or less, and particularly preferably less than 70° C. In the present invention, it has been found that when the temperature at which the microorganisms are aggregated exceeds 70° C., while the cell membrane is damaged and the cytoplasmic matrix flows out, aggregation further proceeds only in the remaining cell membrane. It has been found that this cytoplasmic matrix is hardly separated from the liquid component even by the solid-liquid separation and remains in the liquid component, which as a result generates foaming in the distillation column for extracting the organic substance even if the microorganisms and the dead microorganisms were removed by solid-liquid separation, and there is a possibility that continuous distillation may be hindered. From the viewpoint of performing efficient solid-liquid separation as well as suppressing foaming in the distillation column, the heating temperature of the organic substance-containing liquid is preferably 45° C. or higher and lower than 70° C. and more preferably 50° C. or higher and lower than 60° C.

At the time of heating, the organic substance-containing liquid may be stirred in order to promote aggregation of the microorganisms, etc. The heating time is not particularly limited and is usually about 10 seconds to 30 minutes from the viewpoint of efficiently causing aggregation of the solid component.

The centrifugation operation can be performed using a known centrifugation device. The organic substance-containing liquid is treated with a centrifugation device and then left to stand for a predetermined period of time, whereby a solid component containing the microorganisms and the dead microorganisms, etc. and a liquid component containing the organic substance are separated, and only the liquid component can be extracted as a supernatant liquid.

From the viewpoint of efficiently separating the solid component, the centrifugal acceleration during the centrifugal separation is usually 100 to 10000 G, preferably 200 to 5000 G, more preferably 300 to 3000 G, and particularly preferably 500 to 2000 G.

<Extraction Step>

Next, the organic substance is extracted from the liquid component containing the organic substance obtained through the solid-liquid separation step (see FIG. 1). A desired organic substance can be obtained by this step. Examples of the device used in the extraction step include a distillation device, a treatment device including a pervaporation membrane, a treatment device including a zeolite dehydration membrane, a treatment device for removing a low boiling point substance having a boiling point lower than that of the organic substance, a treatment device for removing a high boiling point substance having a boiling point higher than that of the organic substance, and a treatment device including an ion exchange membrane. These devices may be used alone or two or more in combination. As the unit operation, thermal distillation or membrane separation may be suitably used.

In the thermal distillation, a desired organic substance can be purified with high purity using a distillation device.

The temperature in the still at the time of distillation of the organic substance (particularly ethanol) is not particularly limited, and is preferably 100° C. or less and more preferably about 70 to 95° C. Setting the temperature in the still within the above range will ensure necessary separation of the organic substance from the other components, i.e., distillation (purification) of the organic substance.

The pressure in the distillation device during distillation of the organic substance may be an atmospheric pressure; however, preferred pressure is less than the atmospheric pressure and more preferred is about 60 to 95 kPa (gauge pressure). Setting the pressure in the distillation device within the above range allows improvement of the separation efficiency of the organic substance, which can lead to improvement in the yield of the organic substance. The yield of the organic substance (concentration of the organic substance obtained after distillation) is preferably 90 wt. % or more, more preferably 99 wt. % or more, and particularly preferably 99.5 wt. % or more.

In the membrane separation, a known separation membrane can be used appropriately, for example, a zeolite membrane can be used appropriately.

<Organic Substance and Use Thereof>

Examples of the organic substance obtained by the production method according to the present invention include methanol, ethanol, 2,3-butanediol, acetic acid, lactic acid, isoprene, butadiene, etc., preferably alcohol or diols having 1 to 4 carbons, and more preferably ethanol. The use of the organic substance obtained by the production method of the present invention is not particularly limited. The produced organic substance can be used as a raw material for, for example, plastics, resins, and the like, and can also be used as various solvents, fungicides, or fuels. The high-concentration ethanol can be used as fuel ethanol mixed with gasoline, etc., and can also be used as an additive for cosmetics, beverages, chemical substances, raw materials of fuels (jet fuel), food, etc., having extremely high versatility. Specific uses of ethanol, one example of the organic substance obtained by the production method of the present invention will be described below.

<Use of Ethanol>

Ethanol of the present invention can be used as a raw material for producing various organic compounds. For example, ethanol of the present invention can be used as a raw material for the production of butadiene, ethylene, propylene, isobutene, acetaldehyde, acetic acid, ethyl acetate, methyl (meth) acrylate, ethyl-t-butyl ether ethylene glycol, an ester composition, polyester, acrylic acid, aminohexanoic acid, diethyl carbonate, polyethylene (PE), polyethylene terephthalate (PET), polypropylene (PP), polyisobutylene, polymethylmethacrylate (PMMA), ethylene propylene diene rubber (EPDM), polybutylene terephthalate (PBT), polyethylene furanoate (PEF), polyurethane (PU), and the like. Explained hereunder is a method for synthesizing butadiene using ethanol of the present invention as a raw material and a method for producing polyethylene and polyester by way of example; however, it goes without saying that it can also be used for raw materials for other chemical products and polymers.

<Method for Synthesizing Butadiene>

Butadiene is produced by refining C4 fraction that is subgenerated mainly when synthesizing (i. e., naphtha cracking) ethylene from petroleum, and is a raw material for synthetic rubber. However, there is a need in recent years for a technology for converting ethanol (ethanol derived from microbial fermentation) that is not derived from fossil fuels into 1,3-butadiene, instead of chemical industrial raw materials obtained from petroleum. As a method for synthesizing butadiene using ethanol derived from microbial fermentation as a raw material, there is known a method using MgO as a catalyst, a method using a mixture of $Al_2O_3$ and ZnO, a catalyst having a magnesium silicate structure, and the like. As the catalyst, vanadium, manganese, iron, cobalt, nickel, copper, zinc, gallium, niobium, silver, indium, cerium, and the like are used.

The ethanol of the present invention is brought into contact with the above-mentioned catalyst and heated to cause ethanol conversion reaction, and as a result, 1,3-butadiene can be synthesized. Synthesizing butadiene using ethanol of the present invention as a raw material makes it possible to realize an ultimate resource recycling society independent of petroleum resources.

The heating temperature for accelerating the conversion reaction is, for example, about 300 to 450° C. and preferably 350 to 400° C. in the reaction system. When the temperature in the reaction system falls below the above ranges, the catalyst activity cannot be sufficiently obtained, decreasing the reaction rate, and the production efficiency tends to decrease. On the other hand, if the temperature in the reaction system exceeds the above ranges, the catalyst may be easily deteriorated.

The reaction can be carried out by a conventional method such as a batch method, a semi-batch method, and a continuous method. When the batch or semi-batch method was employed, the conversion rate of ethanol can be increased; however, according to the ethanol of the present invention, it can be converted more efficiently than the conventional types even when the continuous method was employed. This reason is not clear; however, it is considered that the ethanol derived from a circulating resource using gas containing carbon monoxide and hydrogen as a substrate as like the present invention has a characteristic peak which cannot be observed in the ethanol derived from fossil fuels in a gas chromatograph measured by a gas chromatography mass spectrometry.

Examples of the method for bringing the raw material into contact with the catalyst can include a suspended bed method, a fluidized bed method, a fixed bed method, etc. The method may be either a vapor phase method or a liquid phase method. In view of convenience in recovery and regeneration of the catalyst, preferred is the use of a fixed bed reaction device for gas-phase continuous flow in which the catalyst is charged into a reaction tube to form a catalyst layer and the raw material is passed through as a gas in order to react with the gas phase. When the reaction is carried out in the gas phase, the ethanol of the present invention may be gasified and supplied to the reactor without dilution, or may be diluted appropriately with an inert gas such as nitrogen, helium, argon, carbon dioxide, etc. and supplied to the reactor.

After completion of the ethanol conversion reaction, the reaction product (1,3-butadiene) can be separated and purified by separation means such as filtration, concentration, distillation, extraction, or a combination thereof.

<Polyethylene>

The ethanol of the present invention can also be suitably used as a raw material for polyethylene, which is widely used as a universal plastic. Conventional polyethylene was produced by synthesizing ethylene from petroleum and polymerizing the ethylene monomer. By producing polyethylene using the ethanol of the present invention, it is possible to realize an ultimate resource recycling society independent of petroleum resources.

First, using ethanol according to the present invention as a raw material, ethylene is synthesized, which is a raw material for polyethylene. The method for producing ethylene is not particularly limited, and it can be obtained by a conventionally known method, and as one example, ethylene can be obtained by dehydration reaction of ethanol. Although a catalyst is usually used when ethylene is obtained by the dehydration reaction of ethanol, this catalyst is not particularly limited, and those conventionally known can be used. Advantageous in the method is a fixed bed flow reaction in which the catalyst and the product are easily separated, and γ-alumina is preferred, for example.

Since the dehydration reaction is an endothermic reaction, it is usually carried out under heating conditions. If the reaction proceeds at a commercially useful reaction rate, the heating temperature is not limited, and is preferably 100° C. or higher, more preferably 250° C. or higher, and further preferably 300° C. or higher. The upper limit is also not particularly limited, and is preferably 500° C. or lower and more preferably 400° C. or lower from the viewpoint of energy balance and equipment.

The reaction pressure is not particularly limited, and preferred is a pressure equal to or higher than the normal pressure, in order to facilitate the subsequent gas-liquid separation. A fixed bed flow reaction in which the catalyst is easily separated is suitable from the industrial viewpoint; however, reaction may be possible with a liquid phase suspended bed, a fluidized bed, or the like.

In the dehydration reaction of ethanol, the yield of reaction depends on the amount of water contained in the ethanol supplied as a raw material. Generally, when the dehydration reaction is carried out, it is preferable that there is no water in view of efficiency in water removal. However, in the case of the dehydration reaction of ethanol using a solid catalyst, the amount of other olefins, particularly butene, produced tends to increase in the absence of water. The lower limit of the allowable water content is 0.1 mass % or more and preferably 0.5 mass % or more is necessary. The upper limit is not particularly limited; however preferably is 50 mass % or less, more preferably 30 mass % or less, and further preferably 20 mass % or less from the viewpoint of material balance and heat balance.

By carrying out the dehydration reaction of ethanol as described above, a mixed portion of ethylene, water and a small amount of unreacted ethanol can be obtained, and since ethylene is gas at room temperature under about 5 MPa or less, ethylene can be obtained by removing water and ethanol from these mixed portion by gas-liquid separation. This method may be performed by a known method. Subsequently, the ethylene obtained by the gas-liquid separation is further distilled, and the distillation method, the operating temperature, the residence time, and the like are not particularly limited, except that the operating pressure at this time is not less than the normal pressure.

In the case of ethanol derived from a recycling resource using a gas containing carbon monoxide and hydrogen as a substrate as in the present invention, a characteristic peak which cannot be observed in ethanol derived from fossil fuels exists in a gas chromatograph measured by gas chromatography mass spectrometry. Therefore, ethylene obtained from ethanol is considered to contain trace amounts of impurities. Depending on the use of ethylene, these trace impurities can be problematic and thus may be removed by purification. The purification method is not particularly limited, and can be carried out by a conventionally known method. Suitable purification operation can include, for example, adsorption purification. The adsorbent to be used is not particularly limited, and conventionally known adsorbents can be used. For example, a caustic water treatment may be used in combination as a method for purifying impurities in ethylene. In the case of carrying out caustic water treatment, it is desirable to do so before adsorption purification. In this case, water removal treatment needs to be carried out after the caustic treatment and before the adsorption purification.

The polymerization method of the monomer containing ethylene is not particularly limited, and can be carried out by a conventionally known method. The polymerization temperature and the polymerization pressure may be appropriately adjusted depending on the polymerization method and the polymerization device. The polymerization device is not particularly limited, and a conventionally known device can be used. Hereunder is explained one example of a polymerization method of a monomer containing ethylene.

The polymerization method of polyolefin, in particular, an ethylene polymer or a copolymer of ethylene and α-olefin can be appropriately selected depending on the type of polyethylene to be polymerized, for example, difference in density or branching of high-density polyethylene (HDPE), medium-density polyethylene (MDPE), low-density polyethylene (LDPE), and linear low-density polyethylene (LLDPE). For example, polymerization can be preferably carried out by using a multisite catalyst such as a Ziegler-Natta catalyst or a single-site catalyst such as a metallocene catalyst as the polymerization catalyst and conducting any method of gas phase polymerization, slurry polymerization, solution polymerization and high-pressure ion polymerization, in one step or multi-steps of 2 steps or more.

A single-site catalyst is a catalyst capable of forming a uniform active species, and is usually prepared by bringing a metallocene transition metal compound or a non-metallocene transition metal compound into contact with an activating promoter. A single-site catalyst is preferable as it has a uniform active site structure as compared with the multi-site catalyst and is capable of polymerizing a polymer having a high molecular weight and a high degree of uniformity. As the single-site catalyst, particularly a metallocene catalyst is preferably used. A metallocene catalyst is a catalyst comprising a transition metal compound of Group IV of the periodic table containing a ligand having a cyclopentadienyl skeleton, a promoter, optionally an organic metal compound, and each catalyst component of the carriers.

In a transition metal compound of Group IV of the periodic table including a ligand having a cyclopentadienyl skeleton, such cyclopentadienyl skeleton is a cyclopentadienyl group, a substituted cyclopentadienyl group or the like. The substituted cyclopentadienyl group has a substituent such as a hydrocarbon group having 1 to 30 carbons. Examples of the transition metal include zirconium, titanium, hafnium, etc. and particularly preferred are zirconium and hafnium. The transition metal compound usually has 2 ligands having a cyclopentadienyl skeleton, and each ligand having a cyclopentadienyl skeleton is preferably linked to each other by a bridging group. One of the above-mentioned transition metal compounds can be used as the catalyst component or else a mixture of two or more compounds.

The term "promoter" means a promoter which can make the above-mentioned transition metal compound effective as a polymerization catalyst or can balance ionic charges in a catalytically activated state. Examples of the promoter include a benzene-soluble aluminoxane of an organoaluminum oxy compound, a benzene-insoluble organoaluminum oxy compound, an ion-exchange layered silicate, a boron compound, an ionic compound composed of cation with or without an active hydrogen group and a non-coordinating anion, a lanthanoid salt such as lanthanum oxide, tin oxide, and a phenoxy compound containing a fluoro group.

The above-mentioned transition metal compound may be used by being supported on a carrier of an inorganic or organic compound. The carrier is preferably a porous oxide of an inorganic or organic compound, and specific examples thereof include ion-exchangeable layered silicates such as montmorillonite, $SiO_2$, $Al_2O_3$, $MgO$, $ZrO_2$, $TiO_2$, $B_2O_3$, $CaO$, $ZnO$, $BaO$, $ThO_2$, and mixtures thereof.

Examples of the organometallic compound to be further used as necessary include an organoaluminum compound, an organomagnesium compound, and an organozinc compound. Amongst these, preferred use is made to organic aluminum.

As the polyolefin, a polymer of ethylene or a copolymer of ethylene and α-olefin may be used alone or two or more thereof may be mixed and used.

<Acetaldehyde>

Acetaldehyde is an important chemical as an industrial raw material. Acetaldehyde is useful as a raw material for, for example, acetic acid and ethyl acetate.

Acetaldehyde can be produced by oxidizing ethanol by a known method. For example, ethanol can be oxidized with chlorine to produce acetaldehyde. Chlorine is usually reacted with ethanol in a gaseous state. Chlorine may be supplied in a concentration of about 100%, or it may be supplied by diluting with an inert gas (e.g., nitrogen, helium, neon, argon, etc.). The degree of dilution in this case is 50 wt. % or less and preferably 25 wt. % or less, in consideration of the reaction efficiency. Ethanol and chlorine are preferably reacted with, for example, 100 g of an aqueous ethanol solution at a feed amount of 25 to 100 sccm.

The oxidation of ethanol with chlorine is preferably carried out using a chlorine-containing compound such as chlorine gas, hydrogen chloride, phosphorus pentachloride, phosphorus trichloride, phosphorus oxychloride, thionyl chloride, and a hypochlorous acid compound. This oxidation can be realized, for example, by photoreaction, thermal reaction, catalytic reaction, and the like. Among these, oxidation of ethanol by photochlorination or thermal chlorination with chlorine gas is preferred, and more preferred is oxidation by photochlorination with chlorine gas. Examples of the photoreaction include a method of irradiating light having various wavelengths such as ultraviolet rays and visible rays, and among these, it is preferable to carry out reaction by irradiating light having a wavelength of about 300 to 500 nm from a light source. The light source is not particularly limited, and fluorescent lamps, mercury lamps, halogen lamps, xenon lamps, metal halide lamps, excimer lamps, LED lamps, and the like can be used. The reaction temperature is preferably about 0 to 80° C. and preferably about 0 to 50° C. The suitable reaction time is about 1 to 5 hours.

As another example, acetaldehyde can be produced by oxidizing ethanol in the gas phase in the presence of oxygen molecules and a catalyst. As such catalyst, use can be made to, for example, a base metal oxide in which gold fine particles are dispersed and fixed. Examples of the base metal oxides include $La_2O_3$, $MoO_3$, $Bi_2O_3$, $SrO$, $Y_2O_3$, $MgO$, $BaO$, $WO_3$, $CuO$, and a complex oxide containing one or more thereof.

The oxidation reaction of ethanol is carried out by bringing a gas containing ethanol and oxygen molecules into contact with the catalyst at, for example, 100 to 280° C. The oxygen molecules used in the reaction may be supplied as oxygen gas or air may be used. Also, said gas, the raw material gas, may contain a diluent gas (carrier gas) if necessary. In this case, the device used for the reaction may be a general device which is usually used for the gas-phase reaction. For example, reaction is carried out by filling the catalyst into a reaction tube, feeding a gas containing ethanol and oxygen gas or air into the reaction tube while keeping the reaction tube in a heated state to a predetermined temperature, bringing the raw material gas into contact with the catalyst, and collecting the reaction gas. The reaction pressure may be carried out at normal pressure, and may be pressurized to about 0.5 to 5 Pa (atmospheric pressure) if necessary. As the diluent gas, for example, a so-called inert gas such as nitrogen, argon, helium or carbon dioxide is used. The amount of the diluent gas to be used may be appropriately determined, taking into consideration the composition of the raw material gas, the flow rate, the heat of reaction, and the like, and is preferably 1 to 100 times the volume of usual ethanol.

The ratio of ethanol and oxygen molecules (oxygen gas) fed to the reaction tube is not particularly limited, and is usually 0.5 to 100 vol % of oxygen gas or oxygen gas in the air, preferably 1 to 10 vol %, and more preferably 2 to 5 vol % with respect to ethanol. The amount of the catalyst to be used is not particularly limited, and may be generally about 0.1 to 1.0 g, as long as the inner diameter of the reaction tube is 6 to 10 mm. In practice, it is preferably used in an amount in which the space velocity (SV) is in the range of about 10,000 to 40,000 $hr^{-1} \cdot ml \cdot g_{cat}^{-1}$ in relation to the gas flow rate.

Acetaldehyde can also be produced by dehydrogenation of ethanol in the presence of a catalyst. As such catalyst, use can be made to, for example, a solid catalyst containing copper as an active species. The copper as the active species may be in any form as long as it has an activity of converting ethanol into acetaldehyde, and may be in any form of metallic copper (simple substance) or copper compounds (oxide, hydroxide, copper salts (inorganic acid salts such as copper sulfate, copper phosphate, copper nitrate, and copper carbonate; and organic acid salts such as copper salt of carboxylic acid), and the like). The solid catalyst may contain at least one selected from the group consisting of such copper simple substances and copper compounds. Copper as the active species is preferably in the form of metallic copper. Copper may also be used as it is in the form of metallic copper or a copper compound, or may be used in the form of being supported on a carrier. Copper as the active species may act as a main catalyst of the solid catalyst, and may be used in combination with a promoter and the like. The solid catalyst may be in a form in which both copper and the promoter are supported on a carrier.

Any dehydrogenation reaction may be possible, as long as ethanol can be brought into contact with the solid catalyst, and liquid phase reaction may be possible, and in most cases, gas phase reaction in which gaseous ethanol is brought into contact with a solid catalyst in the gas phase is employed. In view of the equilibrium relationship between ethanol and acetaldehyde, the catalyst life, etc. the temperature may be 150 to 350° C., preferably 170 to 300° C., and more preferably about 200 to 280° C. The higher the reaction temperature, the more the equilibrium shifts to the acetaldehyde side, thus the conversion rate can be improved. The reaction may be carried out under pressure, or may be carried out under normal pressure in view of convenience. It can also be carried out under reduced pressure in view of the advantage of ethanol conversion rate.

<Acetic Acid>

Acetic acid is an important chemical as an industrial raw material. Acetic acid is useful as a raw material for, for example, vinyl acetate monomer, acetic anhydride, acetic ester, and the like.

Acetic acid can be produced by oxidation of acetaldehyde by a conventional method. For example, acetic acid can be produced by air oxidation of acetaldehyde in the presence of a catalyst. Examples of the catalyst include manganese acetate and cobalt acetate.

<Ethyl t-Butyl Ether>

Ethyl-t-butyl ether (ETBE) is an important chemical as an industrial raw material. ETBE is useful as, for example, an alternative fuel to gasoline, particularly as a high-octane fuel.

ETBE can be synthesized from ethanol and isobutene by a conventional method. For example, it can be produced by reacting ethanol and isobutene in the presence of a reaction catalyst. The molar ratio of isobutene to ethanol of the raw material is preferably 0.1 to 10 mol and more preferably 0.5 to 2 mol.

As the reaction catalyst, a cation exchange resin is preferably used, and more preferably a strongly acidic cation exchange resin. Such strongly acidic cation exchange resin is preferably a porous type (MR type) styrene-based resin to which a strong acid group such as a sulfonic acid group ($-SO_3H$) is introduced as an ion exchange group. The particle size of the strongly acidic cation exchange resin is preferably 0.5 to 1.0 mm. The amount of the reaction catalyst used is preferably 1 to 90 g, more preferably 1 to 90 g, and further preferably 4 to 9 g per 1 mol of ethanol.

The use of the reaction catalyst is not particularly limited, and use can be made for reaction in a fixed bed, a fluidized bed, or a suspended bed state. The reaction form of isobutene with ethanol is not particularly limited, and is preferably carried out by a pressurized gas-liquid mixed phase reaction method in which ethanol can maintain a liquid phase. In this case, the yield of ETBE obtained is further improved.

<Ester>

A wide variety of esters can be prepared by reacting ethanol with various carboxylic acids. For example, ethyl benzoate can be obtained from ethanol and benzoic acid, and diethylene glycol, which is a raw material for polyester, can be obtained from ethanol via ethylene. By producing polyethylene using the ethanol of the present invention, it is possible to realize an ultimate resource recycling society independent of petroleum resources.

The polyester comprises a diol unit and a dicarboxylic acid unit, and is obtained by a polycondensation reaction using ethylene glycol as the diol unit, and terephthalic acid and isophthalic acid as the dicarboxylic acid unit. The ethylene glycol is produced from ethanol of the present invention as a raw material, and for example, ethylene glycol can be obtained from ethanol by a conventionally known method such as a method for producing ethylene glycol via ethylene oxide.

As the dicarboxylic acid, an aromatic dicarboxylic acid, an aliphatic dicarboxylic acid, and derivatives thereof can be used without limitation. Examples of the aromatic dicarboxylic acid include terephthalic acid and isophthalic acid, and examples of the aromatic dicarboxylic acid derivative include lower alkyl ester of aromatic dicarboxylic acid, specifically, methyl ester, ethyl ester, propyl ester, butyl ester, and the like. Among these, terephthalic acid is preferred, and dimethyl terephthalate is preferred as the derivative of the aromatic dicarboxylic acid. Specific examples of the aliphatic dicarboxylic acid include linear or alicyclic dicarboxylic acids having usually 2 to 40 carbons, such as oxalic acid, succinic acid, glutaric acid, adipic acid, sebacic acid, dodecanedioic acid, dimer acid, and cyclohexane dicarboxylic acid, and the like. Examples of derivatives of aliphatic dicarboxylic acid include lower alkyl esters such as methyl, ethyl, propyl and butyl esters of the above-described aliphatic dicarboxylic acid, and cyclic acid anhydrides of the above-described aliphatic dicarboxylic acid such as succinic anhydride. Among these, adipic acid, succinic acid, dimer acid or a mixture thereof is preferred, and particularly preferred is a compound mainly composed of succinic acid. More preferred as the derivative of the aliphatic dicarboxylic acid is a methyl ester of adipic acid and succinic acid or a mixture thereof.

Polyester can be obtained by a conventionally known method in which the diol unit and the dicarboxylic acid unit above are polycondensed. Specifically, it can be produced by a general method of melt polymerization such as carrying out esterification reaction and/or transesterification reaction between the dicarboxylic acid component and the diol component as above and then carrying out the polycondensation reaction under reduced pressure, or a known solution heating dehydration condensation method using an organic solvent.

The polycondensation reaction is preferably carried out in the presence of a polymerization catalyst, and examples of the polymerization catalyst include a titanium compound, a zirconium compound, and a germanium compound.

The reaction temperature of the esterification reaction and/or the transesterification reaction between the dicarboxylic acid component and the diol component is usually in the range of 150 to 260° C., and the reaction atmosphere is usually an inert gas atmosphere of nitrogen, argon, and the like.

In the polycondensation reaction step, a chain extender (coupling agent) may be added to the reaction system. After completion of the polycondensation, the chain extender is added to the reaction system in a uniformly molten state without a solvent, and reacted with the polyester obtained by the polycondensation.

The obtained polyester may be subjected to solid-phase polymerization, if necessary, after being solidified, in order to further increase the degree of polymerization or to remove oligomers such as cyclic trimers.

In the manufacturing method of polyester, various additives may be added within the range as long as the characteristics are not impaired, and for example, a plasticizer, an ultraviolet stabilizer, a coloring inhibitor, a matting agent, a deodorizer, a flame retardant, a weather resistant agent, an antistatic agent, a friction reducing agent, a release agent, an antioxidant, an ion exchanger, a coloring pigment, and the like may be added.

The ethanol of the present invention is not limited to the above-described polymer, and can be used as a raw material for various other polymers, and since the molded product of the obtained polymer is a carbon-neutral material, it is possible to realize an ultimate resource recycling society independent of petroleum resources.

<Products Containing Ethanol>

The ethanol according to the present invention can be used not only as the polymer raw material described above, but also in various products. Examples of the products include chemicals such as cosmetics, perfumes, fuels, antifreeze solutions, fungicides, disinfectants, cleaning agents, mold removers, detergents, hair shampoos, soaps, antiperspirants, face wash sheets, solvents, paints, adhesives, diluents, food additives, and the like. By use in these applications, it is possible to exhibit an appropriate effect corresponding to the application.

<Fuel>

The ethanol of the present invention can also be used as a raw material for fuel (for example, jet fuel, kerosene, light oil, gasoline). Since ethanol has a high bactericidal activity, it can also function as a disinfectant for preventing bacteria from growing in a fuel system such as an engine or piping.

According to the Standards of Society of Automotive Engineers of Japan (2006), the concentration of ethanol in fuel ethanol is defined as 99.5 vol % or more. In other countries (e.g., India), the concentration of ethanol in fuel ethanol is also specified to be greater than 99.5 vol %. Therefore, ethanol having a purity of 99.5 to 99.9 vol % can be suitably used in an ethanol exclusive vehicle. Since the fuel ethanol can also be used for purposes other than the ethanol exclusive vehicle, ethanol having a purity of 99.5 to 99.9 vol % is particularly versatile.

The ethanol according to the present invention can also be mixed with gasoline and used as an ethanol-mixed gasoline. The use of ethanol-mixed gasoline can reduce the environmental burden. The ethanol used in the ethanol-blended gasoline has a purity of 92.0 vol % or more, preferably 95.0 vol % or more, and more preferably 99.5 vol % or more.

The content of ethanol in the ethanol-blended gasoline is preferably 1 vol % to 15 vol %, more preferably 2 vol % to 12 vol %, and further preferably 3 vol % to 10 vol %. When the content of ethanol is 1 vol % or more, there is an advantage that the octane number is improved due to blending of ethanol, and when the content is 15 vol % or less, evaporation properties do not significantly change due to the azeotropic phenomenon with other gasoline base materials, thereby ensuring the proper operating properties of a gasoline automobile.

The amount of water in the ethanol-mixed gasoline is preferably 0.01 to 0.9 mass % and more preferably 0.01 to 0.7 mass %. The lower limit of the water content depends on the saturated water content of the gasoline base material and the water content in the ethanol, and is substantially about 0.01 mass %. When the upper limit is 0.9 mass % or less, phase separation can be prevented, and even when phase separation occurs, the gasoline layer enables proper operation of the gasoline engine. The water content can be measured by the "Crude Oil and Petroleum Products—Water Content Test Method" described in JIS K 2275, and for example, a Karl Fischer coulometric titration method can be used.

As the gasoline base material, a commonly used gasoline base material can be optionally used, without particular limitation. Examples of the gasoline base material include light naphtha obtained by atmospheric distillation of crude oil, preferably desulfurized light naphtha obtained by desulfurization of said light naphtha, catalytic reformed gasoline obtained by desulfurization and subsequent catalytic reforming of heavy naphtha, debenzeneized catalytic reformed gasoline obtained by debenzeneizing said catalytic reformed gasoline, debenzeneized light catalytic reformed gasoline, debenzeneized heavy catalytic reformed gasoline, and mixtures thereof, cracked gasoline obtained by catalytic cracking or hydrogenolysis method, light cracked gasoline, heavy cracked gasoline, and mixtures thereof, isomerized gasoline obtained by isomerizing light naphtha, and the like.

In addition, ETBE obtained from ethanol according to the present invention as a raw material can be mixed with gasoline and used as an ETBE-mixed gasoline. The use of ETBE-mixed gasoline can reduce the environmental burden. The content of ETBE in the ETBE-mixed gasoline is preferably 1 vol % to 15 vol %, more preferably 2 vol % to 12 vol %, and further preferably 3 vol % to 10%. When the content of ETBE is 1 vol % or more, there is an advantage that the octane number is improved by blending ETBE, and when the content is 15 vol % or less, evaporation properties do not significantly change due to the azeotropic phenomenon with other gasoline base materials, thereby ensuring the proper operating properties of a gasoline automobile.

EXAMPLES

The present invention will be described in more details with reference to Examples; however, the present invention is not limited to the following Examples to the extent the scope of the invention is not exceeded.
<Analysis Method>
In the following examples, the number of active microorganisms in the microbial fermenting vessel was determined by analysis using a flow cytometer (CytoFLEX S, manufactured by Beckman Coulter).

Example 1

A continuous fermenter (fermenting vessel) provided with a main reactor, a syngas supply hole, a medium supply hole, and a discharge hole was filled with a seed bacteria of *Clostridium autoethanogenum* (microorganism) and a liquid culture medium (containing an appropriate amount of a phosphorus compound, a nitrogen compound, various minerals, and the like) for culturing the bacteria.

Next, a syngas composed of 30 vol % of carbon monoxide, 10 vol % of carbon dioxide, 35 vol % of hydrogen and 25 vol % of nitrogen was prepared, fed into the continuous fermenter, and culture (microbial fermentation) was carried out at 37° C.

After the culture, the organic substance-containing liquid discharged from the microbial fermenting vessel was collected. The obtained organic substance-containing liquid was a suspension containing ethanol, microorganisms, dead microorganisms, and the like.

The obtained organic substance-containing liquid 1 was heated to 75° C. and then supplied to a centrifugal device (a desk top centrifugation device manufactured by Mitsubishi Kakoki Kaisha, Ltd.), and centrifugal operation was carried out at a centrifugal acceleration of 1000 G for 1 minute.

Thereafter, the centrifuged solution was left to stand at room temperature overnight, and the organic substance-containing solution was visually observed. As a result, phase separation had occurred between the precipitate consisting of the solid component and the transparent supernatant (liquid component).

The supernatant liquid was collected from the solution after the centrifugation, and distillation was carried out under atmospheric pressure boiling condition (about 100° C.) for 1 hour. As a result, it was possible to extract ethanol; however, a small amount of foam was observed in the supernatant liquid which was subjected to the distillation.

Comparative Example 1

Centrifugation was performed in the same manner as in Example 1, except that the heating temperature of the organic substance-containing liquid 1 was set to 37° C., which was the same as the temperature of the microbial fermenting vessel, and the centrifuged solution was left to stand overnight and then visually observed.

As a result, phase separation was not seen and the entire solution remained as a suspension. This suspension was distilled for 1 hour under normal pressure boiling conditions (about 100° C.); however, distillation was ceased since the suspension started foaming and bubbles reached the upper end of the distillation column.

From the results above, the solid component could not be separated from the organic substance-containing liquid even when the organic substance-containing liquid containing the microorganisms was directly subjected to the centrifugation device since the microorganisms lacked sufficient weight; however, it was found that phase separation between the solid component and the liquid component occurred and solid-liquid separation was possible when the organic substance-containing liquid containing the microorganisms was treated with the centrifugation device after being subjected to heat treatment as like in Example 1. In addition, the foaming of the supernatant liquid during distillation in Example 1 was considered to be due to the fact that the intracellular matrix of the *Clostridium* bacteria flow out of the cells when the bacteria were heated at a high temperature, and thus the intracellular matrix was contained in the supernatant liquid obtained by solid-liquid separation.

Reference Example 1 (Working Example)

To a continuous fermentation device (microbial fermenting vessel) having the same reactor, syngas supply hole, medium supply hole, and discharge hole as in Example 1, were charged seed bacteria of *Clostridium autoethanogenum* (microorganisms) and a liquid culture medium for culturing the bacteria (containing an appropriate amount of a phosphorus compound, a nitrogen compound, various minerals, and the like).

Next, to the continuous fermentation device as above were fed continuously a syngas comprising 30 vol % of carbon monoxide, 10 vol % of carbon dioxide, 35 vol % of hydrogen, and 25 vol % of nitrogen, and the microorganisms were cultured, and when the amount of ethanol production was stabilized, the syngas which was fed to the continuous fermentation device was switched to a life sustaining gas comprising 100 vol % of carbon dioxide, and the number of active microorganisms in the continuous fermentation device was measured by flow cytometry analysis immediately after the switching of the gas. The feed amount of the life sustaining gas was 1/10 of the supply amount of the syngas. Weighing was ceased when 19 hours elapsed from gas switching since the number of active microorganisms reached 40% of the number of active microorganisms immediately after the supply gas was suspended.

Reference Example 2 (Working Example)

Microorganisms were cultured in the same manner as in Reference Example 1. Off-gas discharged from the continuous fermentation device during the culture was collected in a storage tank. When the amount of ethanol production was stabilized, the composition of the off-gas collected in the storage tank was examined and found to be 6 vol % of carbon monoxide, 23 vol % of hydrogen, 34 vol % of carbon dioxide, and 37 vol % of nitrogen.

Subsequently, in the same manner as in Reference Example 1, the syngas which had been fed to the continuous fermentation device was switched to the off-gas collected in the storage tank, and the number of active microorganisms in the continuous fermentation device was measured by flow cytometry analysis immediately after switching of the gas. The feed amount of the off-gas (life sustaining gas) was 1/10 of the feed amount of the syngas. Weighing was ceased when 25 hours elapsed from gas switching since the number of active microorganisms reached 40% of the number of active microorganisms immediately after the supply gas was suspended.

Figure 3:
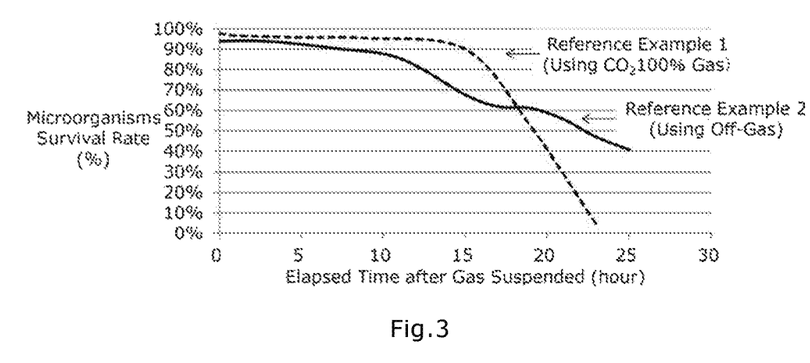
FIG. 3 is a graph expressing the number of active microorganisms over time after the syngas supply was suspended in Reference Examples 1 and 2.

The composition of the life sustaining gas switched from the syngas and the time until the number of active microorganisms in the continuous fermentation device after the switching of the gas decreased to 40% in Reference Examples 1 and 2 are summarized in Table 1 below. The change in number of active microorganisms of Reference Examples 1 and 2 over time is shown in FIG. 3. The vertical axis of the graph in FIG. 3 (number of microorganisms remaining) represents the number of active microorganisms at each time with respect to the number of active microorganisms when the feed of syngas was suspended, expressed in percentage.

TABLE 1

|  | Composition of Life Sustaining Gas (vol %) | | | | Time until number of Microorganisms |
| --- | --- | --- | --- | --- | --- |
|  | $CO_2$ | CO | $H_2$ | $N_2$ | Decreased to 40% |
| Reference Example 1 | 100 | 0 | 0 | 0 | 19 hours |
| Reference Example 2 | 34 | 6 | 23 | 37 | 25 hours |

The invention claimed is:

1. A method for producing an organic substance from a syngas comprising carbon monoxide by microbial fermentation, comprising:
   feeding the syngas to a microbial fermenting vessel and fermenting the syngas with microorganisms to obtain an organic substance-containing liquid, wherein the microorganisms comprise a *Clostridium* microorganism,
   heating the organic substance-containing liquid to a temperature of 45° C. or higher but less than 70° C.,
   centrifuging the organic substance-containing liquid to separate the organic substance-containing liquid into a solid component containing the microorganisms and a liquid component containing the organic substance, and
   extracting the organic substance from the liquid component by thermal distillation at a temperature of 100° C. or less.

2. The method according to claim 1, wherein the syngas is obtained by gasifying a carbon source.

3. The method according to claim 2, wherein the carbon source is waste.

4. The method according to claim 1, wherein the organic substance contains an alcohol having 1 to 6 carbons.

5. The method according to claim 1, wherein the centrifuging is performed at a centrifugal acceleration of 100 to 10000 G.

* * * * *

UNITED STATES PATENT AND TRADEMARK OFFICE
CERTIFICATE OF CORRECTION

PATENT NO. : 11,566,267 B2
APPLICATION NO. : 16/981076
DATED : January 31, 2023
INVENTOR(S) : Satoshi Shimizu et al.

It is certified that error appears in the above-identified patent and that said Letters Patent is hereby corrected as shown below:

On the Title Page

Items (73) and (22) should appear as follows:

(73) Assignee: SEKISUI CHEMICAL CO., LTD.,
Osaka (JP)

(22) PCT Filed: Mar. 22, 2019

Signed and Sealed this
Twenty-fifth Day of July, 2023

Katherine Kelly Vidal
*Director of the United States Patent and Trademark Office*